US012741020B2

(12) United States Patent
Fu et al.

(10) Patent No.: US 12,741,020 B2
(45) Date of Patent: Sep. 22, 2026

(54) METHOD FOR ESTABLISHING EPICUTANEOUSLY SENSITIZED FOOD ALLERGY ANIMAL MODEL

(71) Applicant: Zhejiang Gongshang University, Hangzhou (CN)

(72) Inventors: Linglin Fu, Hangzhou (CN); Qiaozhi Zhang, Hangzhou (CN); Jinru Zhou, Hangzhou (CN); Gang Yu, Hangzhou (CN); Chong Wang, Hangzhou (CN)

(73) Assignee: Zhejiang Gongshang University, Hangzhou (CN)

( * ) Notice: Subject to any disclaimer, the term of this patent is extended or adjusted under 35 U.S.C. 154(b) by 773 days.

(21) Appl. No.: 18/070,833

(22) Filed: Nov. 29, 2022

(65) Prior Publication Data

US 2023/0141616 A1 May 11, 2023

(51) Int. Cl.
*A61K 39/35* (2006.01)

(52) U.S. Cl.
CPC .................................... *A61K 39/35* (2013.01)

(58) Field of Classification Search
None
See application file for complete search history.

(56) References Cited

PUBLICATIONS

Noti et al. Exposure to food allergens through inflamed skin promotes intestinal food allergy through the thymic stromal lymphopoietin-basophil axis. J Allergy Clin Immunol. May 2014;133(5):1390-9, 1399.e1-6. doi: 10.1016/j.jaci.2014.01.021. (Year: 2014).*

Liu et al. Current advances of murine models for food allergy. Mol Immunol. Feb. 2016;70:104-17. doi: 10.1016/j.molimm.2015.11.011. (Year: 2016).*

Kawasaki et al. Skin inflammation exacerbates food allergy symptoms in epicutaneously sensitized mice. Allergy. 2018;73:1313-1321. https://doi.org/10.1111/all.13404. (Year: 2018).*

* cited by examiner

*Primary Examiner* — Robert A Wax
*Assistant Examiner* — Julia A Rossi

(57) ABSTRACT

A method for establishing an epicutaneously sensitized food allergy animal model and belongs to the technical field of medical evaluation and detection. The method includes an allergen sensitization stage and an allergen challenge stage, wherein an MC903 ethanol solution containing OVA is smeared on the skin of experimental animals in the allergen sensitization stage, and the OVA dissolved in a buffer solution is used for an oral challenge in the allergen challenge stage.

4 Claims, 2 Drawing Sheets

METHOD FOR ESTABLISHING EPICUTANEOUSLY SENSITIZED FOOD ALLERGY ANIMAL MODEL

CROSS REFERENCE TO RELATED APPLICATIONS

This application claims the benefit of and the priority from Chinese Patent Application No. 202111331110.2, filed Nov. 11, 2021, which is incorporated herein by reference.

BACKGROUND OF THE INVENTION

Food allergies refer to an abnormal reaction of a body's immune system to certain food proteins that can affect multiple systems in the whole body at the onset, such as the skin, respiratory tract, gastrointestinal tract, and central nervous system, and can lead to anaphylactic shock and be even life-threatening in severe cases. In recent years, the incidence of food allergies has been increasing all over the world, and food allergies have become a public health problem of global concern, also known as the "second" allergy epidemic following asthma. Many studies have found that early skin exposure is an important risk factor for inducing a food allergy. Based on this, the proposed "hypothesis of dual allergen exposure" believes that oral sensitization can promote the formation of immune tolerance, but skin sensitization interferes with oral tolerance. Early exposure to allergens and persistent inflammation resulting from a damaged skin barrier may induce and aggravate food allergies.

An accurate evaluation method of food allergens is helpful for the study of allergy-related immune mechanisms, as well as a necessary approach to develop methods for preventing and treating food allergies. Methods for evaluating the sensitization of food allergens include in vitro immunological methods, simulated gastrointestinal digestion models, cellular models, and animal models. In vivo evaluation is the most direct and accurate method to study the potential sensitization of food. The method of the in vivo evaluation on allergens uses rodent allergy models. Mice are the most commonly used experimental animals in the biomedical field and are often used to establish food allergy animal models, wherein inbred BALB/c mice and C57BL/6 mice are common experimental animals.

At present, the food allergy models established using mice are mostly sensitized by intragastric administration and intraperitoneal injection. However, the intragastric administration-sensitized food allergy model requires a long modeling period, has a high cost, and induces oral tolerance. Intraperitoneal injection is not a natural way for a human body to ingest food allergens, so it cannot reflect the real situation of food entering the body. In recent years, the incidence of food allergy induced by skin sensitization has been increasing year by year. The models established by traditional intragastric administration sensitization and intraperitoneal injection cannot simulate the current sensitization process in clinic.

Therefore, the establishment of an alternative approach to discover the allergic mechanism and study allergies in the human body is desired.

SUMMARY OF THE INVENTION

In order to solve the above-mentioned problems, the present invention provides methods for the establishment and immune evaluation of an epicutaneously sensitized food allergy mice model. The model includes significant sensitization and significant allergy-related indicators.

In the embodiments of the present disclosure, an epicutaneously sensitized food allergy model is established, and two different varieties of mice are selected; on the other hand, the indicators related to the food allergy are analyzed and the epicutaneously sensitized food allergy model is evaluated.

According to the method for establishing an epicutaneously sensitized food allergy model in mice in an embodiment of the present invention, the reagents required for modeling are MC903 (calcipotriol monohydrate) and OVA (ovalbumin). The epicutaneously sensitized food allergy mouse model has a higher allergic symptom score, a higher level of OVA-specific IgE in serum, and a higher proportion of Th2 subsets in the spleen. These results show that the epicutaneously sensitized food allergy mouse model is successfully established and can be used to evaluate the state and degree of food allergy in mice.

The present disclosure provides a method for establishing an epicutaneously sensitized food allergy animal model, including an allergen sensitization stage and an allergen challenge stage, wherein an MC903 ethanol solution containing OVA is smeared on the skin of experimental animals in the allergen sensitization stage, and the OVA dissolved in a buffer solution is used for intragastric administration in the allergen challenge stage.

Preferably, a concentration of OVA is 5 mg/mL, and a concentration of MC903 is 0.1 mM.

In one embodiment, the experimental animals are mice, and the two strains of BALB/c and C57BL/6 mice are being used in the present study.

In one embodiment, the MC903 ethanol solution containing OVA is smeared every day for a total of 2 weeks in the allergen sensitization stage.

In one embodiment, when the MC903 ethanol solution containing OVA is smeared in the allergen sensitization stage, the MC903 ethanol solution containing OVA is smeared on both ears for sensitization.

In one embodiment, when the MC903 ethanol solution containing OVA is smeared in the allergen sensitization stage, the smearing volume is 20 μL for each mouse every time.

In one embodiment, during the intragastric administration in the allergen challenge stage, the concentration of the OVA for the oral challenge of each mouse is 250 mg/mL, and an intragastric administration volume is 200 μL.

In one embodiment, the intragastric administration is performed once on Days 1 and 4.5 after the end of the allergen sensitization phase, respectively.

The present invention has the following beneficial effects: the present invention provides a method for establishing an epicutaneously sensitized food allergy animal model, which has the advantages of simple operation, a short modeling period, low cost, and good reproducibility. The established allergy model has a higher allergic symptom score, a higher level of OVA-specific IgE in serum, and a higher proportion of Th2 subpopulation in the spleen. The epicutaneously sensitized food allergy mouse model is successfully established and can be used to evaluate the state and degree of food allergy in mice.

DETAILED DESCRIPTION OF THE INVENTION

Figure 1:
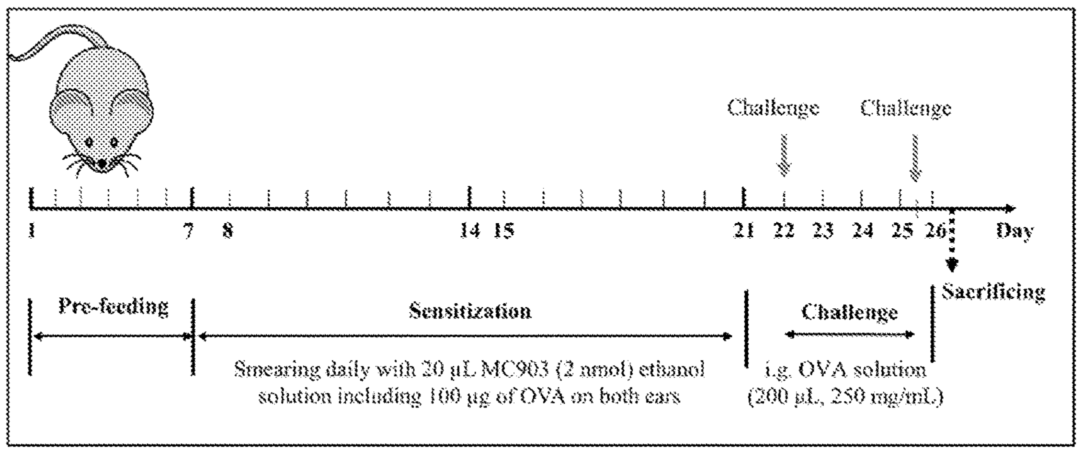
FIG. 1 is a schematic diagram of establishing an epicutaneously sensitized food allergy mouse model.

The modeling period and modeling cost between the intragastric administration-sensitized food allergy mouse model and the epicutaneously sensitized food allergy mouse model are compared in the following embodiments. For the convenience of comparison, the mice selected in the embodiments are BALB/c mice. The results in FIG. 1 show that the modeling period of an intragastric administration-sensitized food allergy model is 33 days, the modeling cost is about RMB 730 yuan per mouse; the modeling period of an epicutaneously sensitized food allergy model is 25 days, and the modeling cost is about RMB 216.5 yuan per mouse. Compared with the traditional intragastric administration-sensitized food allergy model, the epicutaneously sensitized food allergy animal model has the advantages of simple operation, a short modeling period, low cost, and good reproducibility.

In the following embodiments and comparative examples, the clinical allergic symptom scoring is performed on the mice that are last challenged.

The clinical allergic symptom scoring system is shown in the table below:

TABLE 1

Clinical Allergic Symptom Scoring System

| Score | Description |
|---|---|
| | **Scratching** |
| 0 | No symptoms |
| 1 | Mild scratching; rubbing of nose, head, or feet (<5 episodes) |
| 2 | Intermediate scratching; rubbing of nose, head, or feet (>5 to <10 episodes) |
| 3 | Severe scratching (>10 episodes) |
| | **Behavior** |
| 0 | Normal |
| 1 | Hyperactivity |
| 2 | Aggressive behavior; pain loud after prodding |
| | **Physical appearance** |
| 0 | Normal activity |
| 2 | Significantly reduced mobility: piloerection |
| 3 | Immobility after prodding, tremors, and/or significant respiratory distress |
| | **Stool consistency** |
| 0 | Normal |
| 2 | Loose stool |
| 4 | Diarrhea |

In the following embodiments and comparative example, blood of mice is collected through the eyeballs 24 hours after the last challenge, and then the OVA-specific IgE in serum is determined. The specific method is as follows:

Determination of OVA-Specific IgE in the Serum of Mice

1) An OVA solution (100 μg/mL, dissolved in PBS, pH=7.4) is added onto a 96-well ELISA plate according to 100 μL/well, and then the plate is sealed, incubated, and coated overnight at 4° C.
2) Twenty-four (24) hours later, the coated 96-well plate is taken out, the coating solution is discarded, 300 μL of washing solution (PBS+0.05% Tween 20) is added to each well, and the plate is incubated for 1 min; the liquid is discarded, and the plate is dried on filter paper by patting; then 300 μL of washing solution is added to wash the plate, and the plate washing is repeated 3 times to avoid air bubbles.
3) A 200 μL of blocking solution (PBS containing 5% BSA, pH=7.4) is added to each well, and the plate is incubated at 37° C. for 1 h; then 300 μL of washing solution is added to wash the plate 3 times.
4) 100 μL of diluted mouse serum sample is added to each well, and the plate is incubated at 37° C. for 2 h; then 300 μL of washing solution is similarly added to wash the plate 5 times.
5) 100 μL of goat anti-mouse IgE-HRP is added to each well, and the plate is incubated at 37° C. for 1 h; then 300 μL of washing solution is added to wash the plate 5 times.
6) 100 μL of TMB is added to each well, and the plate is incubated 37° C. in the dark for 20 min; then 50 μL of stop solution (2 M $H_2SO_4$) is added, and the OD value of each well is measured at a wavelength of 450 nm.

In the following embodiments and comparative example, the mice are sacrificed by cervical dislocation and dissected to harvest the spleen tissue twenty-four (24) hours after the last challenge, and a proportion of Th2 lymphocyte subpopulation in the spleen tissue is determined. The specific method is as follows:

Preparation of Single-Cell Suspension

1) Organ harvesting: the sacrificed mice are soaked in 75% ethanol for 5 min, then transferred to an ultra-clean table, and dissected to harvest the spleen, mesenteric lymph nodes, and Peyer's patches.
2) Grinding and preparation of single-cell suspension: a 200-mesh sieve is placed on a sterile petri dish, the spleen is placed on the 200-mesh sieve with sterile tweezers, 2-3 mL of a sterile PBS buffer solution is firstly added, and followed by gently grinding, then 7-8 mL of the PBS buffer solution is added and followed by thoroughly grinding and washing the 200-mesh sieve, the spleen cell suspension is transferred into a 15 mL centrifuge tube (do not mix any connective tissue into the cell suspension when transferring). The cell suspension is centrifuged at 1,000 rpm for 5 min at 4° C., and the supernatant is discarded to collect the precipitate.
3) Lysis of red blood cells: about 3 mL of red blood cell lysate is added to each 15 mL centrifuge tube, and the centrifuge tubes are gently vibrated and kept standing at room temperature for 5 min.
4) Centrifugation and washing: The mixture is centrifuged at 1,000 rpm for 5 min at 4° C. 5 mL of PBS buffer solution is added to the cell precipitate, followed by gentle blowing and beating. Centrifugation is performed, and the supernatant is discarded to collect the precipitate; this operation is repeated 2 times.
5) Counting: about 1 mL of RPMI-1640 medium (1% penicillin and 10% fetal bovine serum) is added to the cell precipitate, resuspension by blowing and beating is performed, and cells are adjusted to $10^6$-$10^7$ cells/mL after counting.

Flow Cytometry 1) 1 mL of spleen single-cell suspension is transferred into a 1.5 mL EP tube, centrifugation is performed at 500 rpm for 5 min at 4° C., and the supernatant is discarded. Surface antibodies (FITC-conjugated anti-mouse-CD4 monoclonal antibody) are added, and the tube is incubated at 4° C. in the dark for 30 min. In addition, one single staining tube is prepared for each antibody; a blank tube without adding any antibody is prepared for each group.
2) 1 mL of staining buffer solution is added for washing, centrifugation is performed at 500 rpm for 5 min at 4° C., and the supernatant is discarded
3) 250 μL of 1×Fix/Perm buffer solution is added, the solution is mixed well, and the tube is incubated at 4° C. in the dark for 30 min.
4) 1×Perm/Wash Buffer solution is added for washing, centrifugation is performed at 500 rpm for 5 min at 4° C., and the supernatant is discarded. The operation is repeated once.
5) 100 μL of 1×Perm/Wash buffer solution and intracellular antibodies (PE-conjugated anti-mouse IL4 monoclonal antibody) is added, the solution is mixed well, and the tube is incubated at 4° C. in the dark for 60 min.
6) After washing 2 times, 500 μL of stain buffer solution is added to the cell precipitate, and the solution is mixed well and analyzed by a flow cytometer.

Example 1

FIG. 1 depicts the schematic representation of a protocol for establishing an allergy mouse model. BALB/c mice are purchased from Zhejiang Academy of Medical Sciences (No. 182, Tianmushan Road, Xihu District, Hangzhou City, Zhejiang Province), and Zhejiang Academy of Medical Sciences fed the mice and performed the relevant experimental operations. After the mice were pre-fed for 1 week, those weighing 18±1 g were used for subsequent experiments. After grouping, the mice are sensitized by smearing the MC903 (2 nmol) ethanol solution containing OVA on both ears, a smearing amount was 20 μL, and the sensitization lasted for 2 weeks. After the sensitization, the mice are challenged by intragastric administration with the PBS solution containing OVA (50 mg) on the morning of Day 1 and at the noon of Day 4, respectively, and the OVA for intragastric administration is dissolved in a PBS solution (pH=7.4), a concentration is 250 g/L, and a volume of intragastric administration is 200 μL for each mouse. The symptoms of the mice are recorded within 30 min after each challenge and used for allergic symptom scoring. Blood of the mice is collected 24 hours after the last challenge, and serum is isolated to detect the OVA-specific IgE in serum. After blood collection, the mice are sacrificed by cervical dislocation, the spleen tissue is collected, and a proportion of the Th2 lymphocyte subpopulation in the mouse spleen single-cell suspension is analyzed by using a flow cytometer. The results of the clinical symptom score, the OVA-specific IgE in the serum, and the proportion of Th2 lymphocyte subpopulation in spleen tissue are analyzed to evaluate the advantages and disadvantages of the epicutaneously sensitized animal models.

The mice in the treatment group are mice that were sensitized by smearing the MC903 (2 nmol) ethanol solution containing OVA (100 μg) on both ears; and the mice in the blank group are mice that are treated by smearing an OVA (100 with a smearing amount of 20 μL) ethanol solution. The results are of this Example shown in FIG. 2-FIG. 4.

Figure 2:
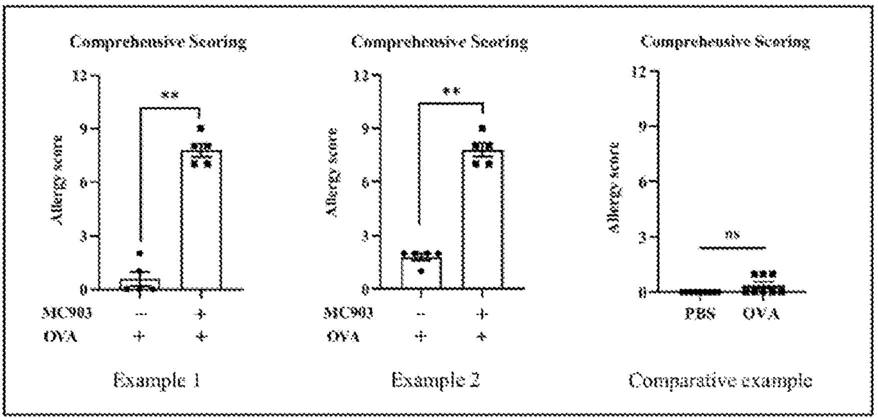
FIG. 2 depicts the comprehensive scoring of clinical allergic symptoms in mice, wherein "+" represents "presence", and "−" represents "absence"

The clinical allergic symptom score is shown in FIG. 2: the clinical allergic symptom score within 30 min after the challenge of the mice in the treatment group is 8.20±0.20, significantly higher than that of the mice in the blank group (0.80±0.23).

Figure 3:
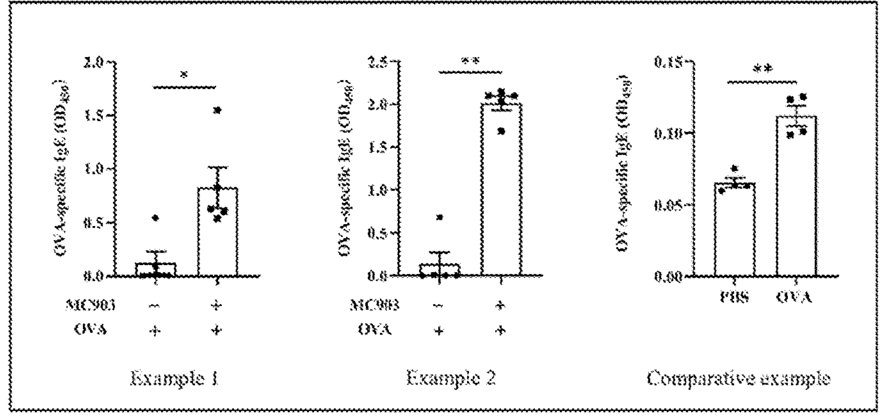
FIG. 3 depicts OVA-specific IgE levels in the serum of mice, wherein "+" represents "presence", and "−" represents "absence"

The level of OVA-specific IgE in serum is shown in FIG. 3: the level of OVA-specific IgE in the serum of the mice in the treatment group ($OD_{450}$=0.82±0.07) is significantly higher than the level of OVA-specific IgE in the serum of the mice in the blank group ($OD_{450}$=0.13±0.04).

Figure 4:
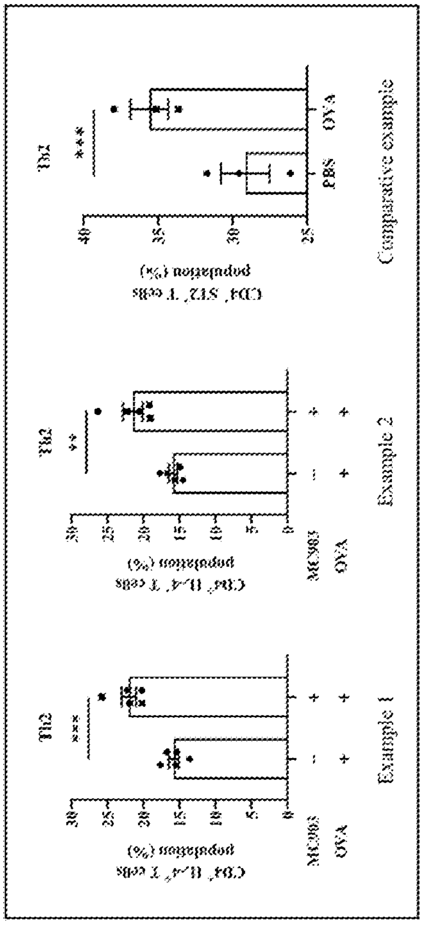
FIG. 4 depicts the results of a proportion of T;h2 lymphocyte subpopulation in spleen tissues of mice, wherein "+" represents "presence", and "−" represents "absence"

The proportion of Th2 lymphocyte subpopulation in spleen tissue is shown in FIG. 4: the proportion of Th2 lymphocyte subpopulation in the spleen of the mice in the treatment group (22.04±0.41%) is significantly higher than the proportion of Th2 lymphocyte subpopulation in the spleen of the mice in the blank group (15.54±1.41%).

After epicutaneous sensitization and oral challenge, the allergy-related indicators (clinical allergic symptom score, level of OVA-specific IgE in the serum, and proportion of Th2 lymphocyte subpopulation in spleen tissue) of the BALB/c mice are all significantly increased so that the epicutaneously sensitized BALB/c mouse model is successfully established.

Example 2

C57BL/6 mice are purchased from Zhejiang Academy of Medical Sciences (No. 182, Tianmushan Road, Xihu District, Hangzhou City, Zhejiang Province), and Zhejiang Academy of Medical Sciences fed the mice and performed the relevant experimental operations. After the mice are pre-fed for 1 week, those weighing 18±1 g are used for subsequent experiments. After grouping, the mice are sensitized by smearing the MC903 (2 nmol) ethanol solution containing OVA on both ears, a smearing amount was 20 μL, and the sensitization lasted for 2 weeks. After the last sensitization, the mice are challenged by intragastric administration with the PBS solution containing OVA (50 mg) on the morning of Day 1 and at the noon of Day 4, respectively, and the OVA for intragastric administration are dissolved in a PBS solution (pH=7.4), a concentration of 250 mg/L, and a volume of intragastric administration is 200 μL for each mouse. The symptoms of the mice are recorded within 30 min after each challenge and used for allergic symptom scoring. Blood of the mice is collected 24 hours after the last challenge, and serum is isolated to detect the OVA-specific IgE in serum. After blood collection, the mice are sacrificed by cervical dislocation, the spleen tissue is collected, and a proportion of the Th2 lymphocyte subpopulation in the mouse spleen single-cell suspension is analyzed by using a flow cytometer. The results of the clinical symptom score, the OVA-specific IgE in the serum, and the proportion of Th2 lymphocyte subpopulation in spleen tissue are analyzed to evaluate the advantages and disadvantages of the epicutaneously sensitized animal models.

The mice are sensitized by smearing the MC903 (2 nmol) ethanol solution containing OVA (100 μg) on both ears; and the mice in a blank group were mice that were treated by smearing an OVA (100 μg, with a smearing amount of 20 μL) ethanol solution. The results are shown in FIG. 2-FIG. 4.

The clinical allergic symptom score is shown in FIG. 2: the clinical allergic symptom score within 30 min after the challenge of the mice in the treatment group is 7.67±0.22, significantly higher than that of the mice in the blank group (1.20±0.08);

The level of OVA-specific IgE in serum is shown in FIG. 3: the level of OVA-specific IgE in the serum of the mice in the treatment group ($OD_{450}$=2.01±0.03) is significantly higher than the level of OVA-specific IgE in the serum of the mice in the blank group ($OD_{450}$=0.14±0.05);

The proportion of Th2 lymphocyte subpopulation in spleen tissue is shown in FIG. 4: the proportion of Th2 lymphocyte subpopulation in the spleen of the mice in the treatment group (21.47±0.54%) is significantly higher than the proportion of Th2 lymphocyte subpopulation in the spleen of the mice in the blank group (15.88±0.24%).

These results indicate that after epicutaneous sensitization and oral challenge, the allergy-related indicators (clinical allergic symptom score, level of OVA-specific IgE in the serum, and proportion of Th2 lymphocyte subpopulation in spleen tissue) of the C57BL/6 mice are all significantly increased so that the epicutaneously sensitized C57BL/6 mouse model is successfully established.

Comparative Example 1

BALB/c mice are purchased from Hangzhou Normal University (No. 16, Xuelin Street, Xiasha Higher Education Park, Qiantang District, Hangzhou City, Zhejiang Province), and Hangzhou Normal University fed the mice and performed the relevant experimental operations. After the mice are pre-fed for 1 week, those weighing 18±1 g are used for subsequent experiments. After grouping, the mice in the treated group are treated by intragastric administration on Monday, Tuesday, Thursday and Friday every week, and the mice are sensitized by intragastric administration of 200 μL of OVA-PBS solution (containing 5 mg of OVA and 10 μg of cholera toxin adjuvant). The sensitization stage lasts for 3 weeks. After the last sensitization, the mice are consecutively challenged for 5 days by intragastric administration with a PBS solution containing OVA (50 mg), wherein the OVA for intragastric administration is dissolved in a PBS solution (pH=7.4), a concentration of 250 mg/L, and a volume of intragastric administration is 200 μL for each mouse. The mice in the blank group are treated by intragastric administration with the same volume of PBS solution and cholera toxin (CT) in the sensitization stage, and the challenge stage is the same as that in the sensitization group. The symptoms of the mice are recorded within 30 min after each challenge and used for allergic symptom scoring. Blood of the mice is collected after 24 hours after the last challenge, and serum is isolated to detect the OVA-specific IgE in serum. After blood collection, the mice are sacrificed by cervical dislocation, the spleen tissue is collected, and a proportion of the Th2 lymphocyte subpopulation in the mouse spleen single-cell suspension is analyzed by using a flow cytometer. The results of clinical symptom scores, serum OVA-specific IgE and the proportion of the Th2 lymphocyte subpopulation in spleen tissue are analyzed to evaluate the advantages and disadvantages of the epicutaneously sensitized animal models.

The mice in the treatment group are sensitized by intragastric administration with the OVA solution and the cholera toxin adjuvant; the mice in the blank group are treated with the same amounts of PBS solution and CT in the sensitization stage. The results are shown in FIG. 2-FIG. 4.

The clinical allergic symptom score is shown in FIG. 2: the clinical allergic symptom score within 30 min after challenge of the mice in the treatment group is 0.25±0.46, not significantly different from that of the mice in the blank group (0).

The level of OVA-specific IgE in the serum is shown in FIG. 3: the level of OVA-specific IgE in serum of the mice in the treatment group ($OD_{450}$=0.11±0.01) is significantly higher than the level of OVA-specific IgE in the serum of the mice in the blank group ($OD_{3450}$=0.07±0.01); however, the level of OVA-specific IgE in the serum of the mice in the treatment group ($OD_{450}$=0.11±0.01) in this comparative example is significantly lower than the level of OVA-specific IgE in the serum of the mice in the treatment group ($OD_{450}$=0.82±0.07) in Example 1.

The proportion of Th2 lymphocyte subpopulation in spleen tissue is shown in FIG. 4: the proportion of Th2 lymphocyte subpopulation in the spleen of the mice in the treatment group (35.59±2.19%) was significantly higher than the proportion of Th2 lymphocyte subpopulation in the spleen of the mice in the blank group (29.14±2.83%). In the case of the proportion of Th2 lymphocyte subpopulation in the spleen, the Comparative Example and Example 1 both can characterize food allergy in mice.

After intragastric administration sensitization and challenge, the allergy-related indicators (level of OVA-specific IgE in serum and proportion of Th2 lymphocyte subpopulation in spleen tissue) of the BALB/c mice are all significantly increased. However, the response value of the level of OVA-specific IgE in serum is significantly lower than that of the epicutaneously sensitized and orally challenged mice.

Sensitized animal models can be established from two different inbred strains of mice (BALB/c and C57BL/6) by using the method of the present method. Compared with the previous food allergy models sensitized and challenged by intragastric administration, the epicutaneously sensitized food allergy animal model in the embodiments of the present invention has the advantages of significant allergy-related indicators, a short modeling period, low cost, and good reproducibility.

What is claimed is:

1. A method for establishing an epicutaneously sensitized food allergy animal model, comprising:

an allergen sensitization stage and an allergen challenge stage, wherein an MC903 ethanol solution containing allergens is smeared on the skin of experimental animals in the allergen sensitization stage, wherein the allergens include ovalbumin (OVA), a concentration of OVA in the MC903 ethanol solution is 5 mg/mL, and a concentration of MC903 in the MC903 ethanol solution is 0.1 mM; and the allergens dissolved in a buffer solution is used for intragastric administration in the allergen challenge stage.

2. The method of claim 1, wherein the experimental animals are mice.

3. The method of claim 2, wherein the mice are BALB/c mice.

4. The method of claim 2, wherein the mice are C57BL/6 mice.

* * * * *